United States Patent [19]
Cox

[11] 4,281,651
[45] Aug. 4, 1981

[54] LUNG VENTILATOR
[75] Inventor: Lawrence A. Cox, Epping, England
[73] Assignee: Airco, Inc., Montvale, N.J.
[21] Appl. No.: 61,971
[22] Filed: Jul. 30, 1979
[51] Int. Cl.³ .............................................. A61M 16/00
[52] U.S. Cl. ............................ 128/204.23; 128/205.23
[58] Field of Search ...................... 128/203.14, 203.25, 128/204.22, 204.21, 204.26, 205.24, 204.23, 205.23

[56] References Cited
U.S. PATENT DOCUMENTS 3,768,468 10/1973 Cox .................................. 128/204.21
4,163,450 8/1979 Kirk .................................. 128/204.23

FOREIGN PATENT DOCUMENTS 2353305 6/1977 France ................................. 128/204.21

Primary Examiner—Henry J. Recla
Attorney, Agent, or Firm—Roger M. Rathbun; Larry R. Cassett

[57] ABSTRACT

A lung ventilator particularly adapted for use in weaning patients from dependence thereupon and includes an exhalation conduit through which the gas exhaled by the patient is passed. Both the rate of flow of gas passing through the exhalation conduit during each individual exhalation phase, and the minute volume of exhaled gases are monitored. If, during any given exhalation phase, the minute volume of exhaled gases should fall below a chosen threshold, indicating that the patient fails to breathe adequately, the ventilator is triggered to perform a mandatory ventilation cycle. The ventilator is inhibited from delivering mandatory breaths, however, until the rate of flow of exhaled gas in a given exhalation phase has reduced to the point which indicates that exhalation has ceased.

4 Claims, 1 Drawing Figure

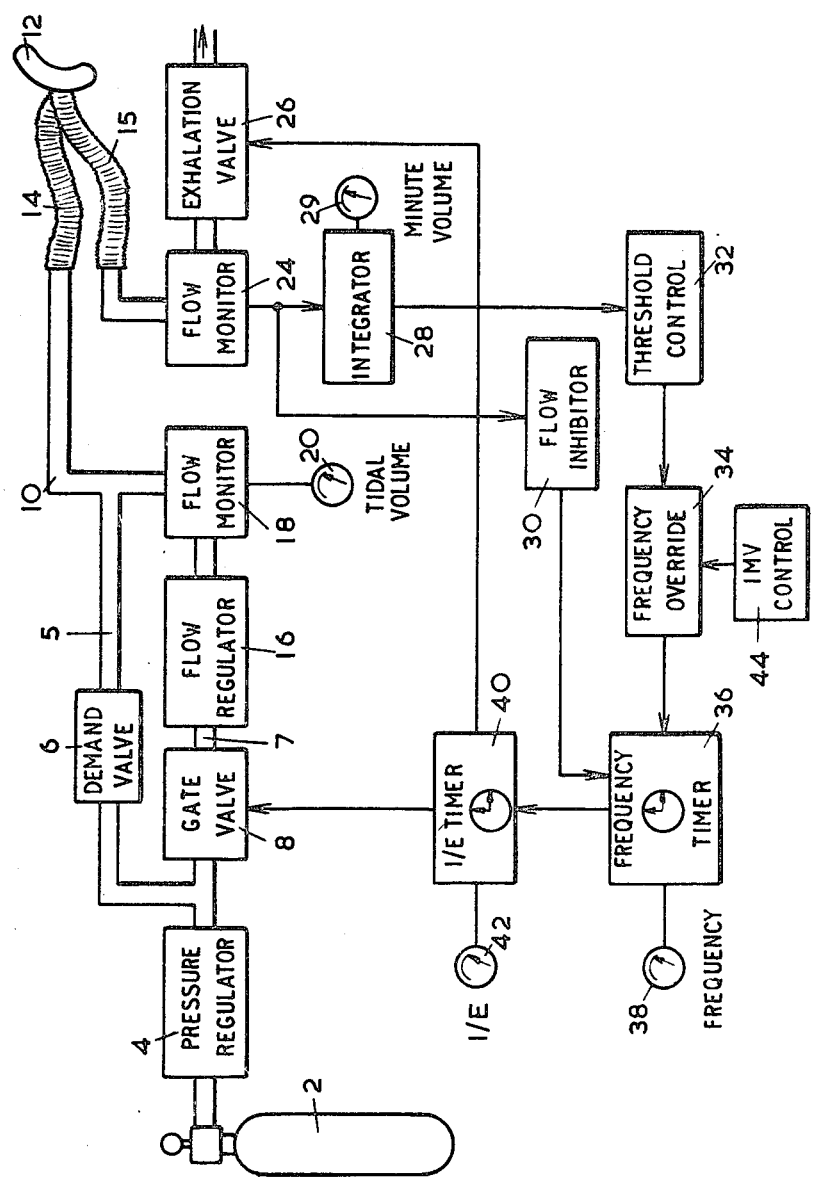

LUNG VENTILATOR

FIELD OF THE INVENTION

This invention relates to lung ventilators, particularly to those used for intensive care, during which the patient is often incapable of breathing voluntarily.

BACKGROUND OF THE INVENTION

When a patient is recovering, it is important to 'wean' him from complete dependence on the ventilator. To effect this, ideally the ventilator should be capable of being operated in a mode in which spontaneous breathing (or ventilation) of a patient is both enabled and encouraged, while his ventilation performance is continually monitored against chosen standards so that the ventilator will revert automatically into its automatic mode should the patient's ventilation deteriorate to an unacceptable extent.

Methods used hitherto do not satisfy this requirement, as the monitoring function has to be carried out concurrently with manual adjustments to the ventilator's controls. Methods have been used in the past whereby the patient's end-tidal carbon dioxide level is monitored and made to adjust the inspired tidal volume automatically but these methods are both complicated and very expensive. Furthermore they have not so far been developed to the point of reliability or of satisfying the clinical requirements for weaning patients.

The present invention aims at providing a lung ventilator in which the minute volume of the exhaled gases is continuously monitored so that whenever a patient ceases to exhale sufficient gas per minute the ventilator automatically takes over from the patient.

SUMMARY OF THE INVENTION

Accordingly the present invention provides a lung ventilator comprising: a conduit through which pass the gases exhaled by a patient during the exhalation phase of each respiratory cycle; means adapted to produce a signal representing the rate of flow of gas passing through said conduit during each exhalation phase; means adapted to produce a signal representing the minute volume of exhaled gases through said conduit; and means responsive to said signals for triggering the start of an automatic ventilation cycle when the minute volume of exhaled gases is below a chosen threshold, and the rate of flow of the exhaled gases in a given exhalation phase has virtually decreased to zero.

BRIEF DESCRIPTION OF THE DRAWING

The accompanying drawing is a schematic block diagram of a preferred embodiment of a ventilator according to the invention.

DESCRIPTION OF THE PREFERRED EMBODIMENT

The ventilator is adapted to have respirable gases fed to it from a cylinder 2 or other suitable source. The gases are supplied at high pressure, and this is reduced to an intermediate pressure by means of a pressure regulator 4. Downstream of the regulator the inspiratory limb of the ventilator splits into two parallel flowpaths 5 and 7 controlled respectively by a demand valve 6 and a gate valve 8. The gate valve 8 is a controlled on-off valve, and the gases which flow through it when it is open have their rate of flow controlled by a regulator 16. The gases which issue from the regulator pass to a flow monitor 18 which is adapted to produce an electrical pulse for each unit volume of gas which passes through the monitor. These pulses are summated and used to drive a tidal volume meter 20.

Downstream of flow monitor 18 the flowpath 7 rejoins flowpath 5 in an outlet conduit 10 which is normally connected to a patient's breathing mask 12 through a length of flexible conduit 14. The mask 12 is designed to enable gases under pressure to be passed into the patient's lungs during the inhalation phase of the respiratory cycle, and to pass back to the ventilator, through a second length of flexible conduit 15 all the gases exhaled by the patient during the exhalation phase. Conduit 15 communicates with the inlet side of a second flow monitor 24 from which the exhaled gases pass to an exhalation valve 26, the outlet of which is connected to the atmosphere.

Similarly to monitor 18, monitor 24 provides a series of pulses of which each represents a unit volume of gases exhaled by the patient. These are fed both to a flow inhibitor 30, of which the function will be described below, and to an integrator 28. The pulses are continuously integrated at 28 and the integrated value displayed on a meter 29 in terms of minute volume of the xhaled gases. The integrated signal is fed also to a threshold control 32. Similarly to gate valve 8, exhalation valve 26 is a controlled on-off valve, and normally the valves 8 and 26 are controlled alternatively, so that if one is open the other is closed, and conversely.

The threshold control 32 is connected to a frequency override 34 and to a frequency timer 36 having as a second input a signal from flow inhibitor 30. A first output from timer 36 is to a frequency meter 38, while a second is to an I/E timer 40, which is effective to control the relative lengths of the inhalation (I) and the exhalation (E) phases of the respiratory cycle. The timer 40 is connected to a meter 42 displaying the current effective I/E ratio.

When a patient is being weaned from the ventilator, the threshold control 32 is set manually to a value corresponding with a desired minimum minute volume for the exhaled gases of the patient who is connected to the ventilator at the time in question.

When the patient is breathing normally, his attempts to inhale are detected by the demand valve 6, which opens to permit fresh respirable gas to by-pass the flowpath 7 and go directly to the patient's lungs. Each time the patient exhales, the gas passes through conduit 15, monitor 24 and valve 26 before being exhausted to the atmosphere. The ventilator is continuously integrating the exhalation phase to measure of the minute volume of exhaled gases, and effectively comparing it with the chosen minimum value. As long as the sensed minute of volume of exhaled gases exceeds the chosen minimum, the timer 36 is inhibited, and the apparatus will not cycle but permit the patient to breathe spontaneously. However, should the patient cease to breathe adequately, this is detected by the integrated signal of integrator 28 indicating that the respective minute volume of exhaled gases is below the chosen minimum set by the threshold control 32. As soon as tis happens, the frequency override 34 is actuated to enable the timer to switch on. This supplies an output signal to timer 40 which is immediately effective to open gate valve 8 and close exhalation valve 26, thus automatically initiating an inhalation phase. At the end of a period dictated by timer 40, the gate valve 8 is closed and the exhalation valve 26 opened, to permit the patient to exhale. These conditions remain for a time dictated by timer 40 in order to preserve the chosen I/E ratio. At the end of this time, a fresh pulse from timer 36 is effective to initiate another cycle (provided that frequency override 34 has not since been actuated to inhibit the timer again). Thus timer 36 can be regarded as controlling the frequency with which the gate valve 8 is opened, while timer 40 controls the length of time for which the gate valve 8 remains open during the respective respiratory cycle.

At the end of the time interval determined by the setting of the timer 36, when the ventilator would normally be switched into the inspiration mode, the patient may still be exhaling. This may be due to the patient suffering from an obstructed lung and/or because the I/E ratio has been set too short, giving insufficient time for the patient's previous exhalation to be complete. In that event, the flow monitor 24 will sense that gas is still being exhaled, and the flow inhibitor 30 will inhibit timer 36 and prevent it from switching the ventilator into the inspiration mode. When the exhaled flow has dropped to a very low level the inhibit signal is removed, and the timer 36 is allowed to switch on.

Following a change over from spontaneous breathing to automatic ventilation as described above the desired minute volume of exhaled gases will, of course, be reestablished and when this has been sensed by the threshold control 32 the frequency override 34 will once more be actuated to inhibit timer 36 and terminate automatic ventilation at the end of the respiratory cycle taking place. If the patient meanwhile has not recovered his spontaneous breathing ability the process will be repeated. Because the threshold control 32 acts upon a signal derived from the continuous integration of the patient's exhaled flowrate there will inevitably be a few seconds delay between his actual minute volume dropping below the threshold value and the initiation of automatic ventilation, and between the minute volume of exhaled gases rising above the threshold value and the termination of automatic ventilation. The degree of hysteresis effectively imparted to the system of the integrator is of value in preventing instability at the switching point between the 'spontaneous' and 'automatic' modes of operation, while the delay in response to an inadequate minute volume of exhaled gases is clearly insufficient to endanger the patient.

In practice the threshold control 32 may be incorporated in the minute volume meter 29. Thus the meter may comprise a conventional moving-pointer analogue microammeter calibrated in volume units, the threshold control including an adjustable pointer which can be set to any desired position on the meter scale. The adjustable pointer is fitted with a photocell sensor which triggers the frequency override 34 to initiate timer 36 and actuates an audio/visual alarm, in the event that the meter pointer indicating minute volume of exhaled gases falls below the level to which the adjustable pointer is set. When the sensed minute volume of exhaled gases subsequently increases and the moving pointer moves up the scale once more its passage past the adjustable pointer is again detected by the photocell and the timer is inhibited and the alarm(s) cancelled in response. A second adjustable pointer may also be provided, which is set to trigger an alarm in the event of an abnormally high minute volume of exhaled gases being indicated by the meter 29.

Lung ventilators are known which have a so-called intermittent mandatory ventilation (IMV) mode. By this is meant that the ventilator can be set to go through an automatic ventilation cycle at intervals chosen by the operator irrespective of the adequacy of the patient's spontaneous breathing attempts. These 'intermittent' cycles reassure the patient that the ventilator is able to take over responsibility for ventilation should the patient's attempts to breathe become inadequate at any time. The ventilator of the present invention may be designed to have an IMV mode, as it can complement the exhalation volume triggered mode of the invention. In the case of the illustrated embodiment this may be achieved by the inclusion of a control 44 to actuate frequency override 34 and initiate the timer 36 at the chosen intervals.

We claim:

1. An improved lung ventilator for use in weaning a patient from dependence thereupon comprising inlet means for connection to a source of respirable gas, outlet means for supplying respirable gas to a patient, said inlet means and outlet means forming part of an inspiratory flow path for the respiratory gas, valve means for controlling the flow of respiratory gas in the flow path for spontaneous breathing cycles, exhalation conduit means through which pass the gases exhaled by a patient during the exhalation phase of each respiratory cycle, means bypassing said valve means for providing an automatic ventilation cycle for assisted breathing; the improvement comprising means adapted to produce a first signal representing the rate of flow of gas passing through said conduit during each exhalation phase; means adapted to provide a second signal representing the minute volume of exhaled gases through said conduit; and means responsive to said signals for triggering the start of said automatic ventilation cycle when, in any given ventilation phase, the minute volume of exhaled gases is below a chosen threshold and the rate of flow of the exhaled gases has virtually decreased to zero.

2. A lung ventilator according to claim 1 wherein the means adapted to produce said first signal comprise a flow monitor positioned in said conduit, and the means adapted to produce said secnd signal comprise means for integrating said first signal.

3. A lung ventilator according to claim 1 comprising: a timer means for initiating and controlling the frequency of automatic ventilation; means responsive to said second signal for inhibiting said timer means from initiating an automatic ventilation cycle when the minute volume of exhaled gases is above the chosen threshold; and means responsive to said first signal for inhibiting said timer from initiating an automatic ventilation cycle before the rate of flow of the exhaled gases in said given exhalation phase has virtually decreased to zero.

4. A lung ventilator according to claim 1 wherein said inspiratory flow path comprises a pair of gas flowpaths extending in parallel from said inlet means to said outlet means; a demand valve in a first of said flow paths to permit spontaneous breathing of the patient; an on-off valve in the second of said flow paths, the opening of which provides the inspiration phase of the automatic ventilation cycle; an on-off valve in said exhalation conduit; and means responsive to said means for providing an automatic ventilation cycle for controlling the operation of said on-off valves such that when one is opened the other is closed and conversely, and such that the valve in the exhalation conduit is closed only during the inspiration phase of the automatic ventilation cycle.

* * * * *